United States Patent
Leuthardt et al.

(10) Patent No.: US 11,241,183 B2
(45) Date of Patent: Feb. 8, 2022

(54) EEG HEADSETS WITH PRECISE AND CONSISTENT ELECTRODE POSITIONING

(71) Applicant: Neurolutions, Inc., Clayton, MO (US)

(72) Inventors: Eric C. Leuthardt, St. Louis, MO (US); Gerwin Schalk, Glenmont, NY (US); Daniel W. Moran, Ballwin, MO (US); Rob Coker, Foristell, MO (US); David Bundy, Leawood, KS (US); Robert R. Ragland, Temecula, CA (US); Peter J. D'Aquanni, Murrieta, CA (US); Thomas Voorhees, San Diego, CA (US); Gilbert L Carlson, Escondido, CA (US)

(73) Assignee: Neurolutions, Inc., Santa Cruz, CA (US)

( * ) Notice: Subject to any disclaimer, the term of this patent is extended or adjusted under 35 U.S.C. 154(b) by 640 days.

(21) Appl. No.: 15/351,045

(22) Filed: Nov. 14, 2016

(65) Prior Publication Data
US 2017/0143228 A1 May 25, 2017

Related U.S. Application Data

(60) Provisional application No. 62/255,238, filed on Nov. 13, 2015.

(51) Int. Cl.
*A61B 5/291* (2021.01)
*A61B 5/00* (2006.01)
(Continued)

(52) U.S. Cl.
CPC .............. *A61B 5/291* (2021.01); *A61B 5/316* (2021.01); *A61B 5/6803* (2013.01); *G06F 3/011* (2013.01)

(58) Field of Classification Search
CPC . A61B 5/04012; A61B 5/0478; A61B 5/6803; A61B 5/0004; A61B 5/31;
(Continued)

(56) References Cited

U.S. PATENT DOCUMENTS 3,998,213 A * 12/1976 Price .................... A61B 5/0424
600/383
4,683,892 A 8/1987 Johansson et al.
(Continued)

FOREIGN PATENT DOCUMENTS

| WO | WO 2013/054472 | 4/2013 |
|---|---|---|
| WO | WO 2014/141213 | 9/2014 |

OTHER PUBLICATIONS

International Search Report and Written Opinion, Application No. PCT/US2016/061853, dated Mar. 3, 2017.
(Continued)

*Primary Examiner* — Thomas A Giuliani
*Assistant Examiner* — Christine A Dedoulis
(74) *Attorney, Agent, or Firm* — Fish & Richardson P.C.

(57) ABSTRACT

This document discloses EEG headset designs that address shortcomings in prior art headsets and also provides headset solutions for new and useful applications utilizing EEG headsets. One such application is brain computer interface (BCI) applications, and more specifically, a BCI application for stroke therapy in which the headset is utilized to obtain ipsilateral brain signals. This document also discloses BCI devices and methods utilizing EEG headsets.

15 Claims, 13 Drawing Sheets

(51) Int. Cl.
*A61B 5/316* (2021.01)
*G06F 3/01* (2006.01)

(58) Field of Classification Search
CPC ..... A61B 5/0006; A61B 5/291; A61B 5/6814; A61B 2018/00839; A61B 2090/502; A61B 2562/0233; G06F 3/011
See application file for complete search history.

(56) References Cited

U.S. PATENT DOCUMENTS

| | | | | |
|---|---|---|---|---|
| 4,928,696 | A * | 5/1990 | Henderson | A61B 5/0478 600/383 |
| 6,097,981 | A | 8/2000 | Freer | |
| 6,381,481 | B1 | 4/2002 | Levendowski et al. | |
| 8,103,328 | B2 | 1/2012 | Turner et al. | |
| 8,165,684 | B2 | 4/2012 | Putz et al. | |
| 9,622,703 | B2 * | 4/2017 | Badower | A61B 5/291 |
| 2005/0107716 | A1 * | 5/2005 | Eaton | A61B 5/0073 600/544 |
| 2007/0093706 | A1 | 4/2007 | Gevins et al. | |
| 2010/0041962 | A1 | 2/2010 | Causevic et al. | |
| 2011/0015503 | A1 | 1/2011 | Joffe et al. | |
| 2013/0172721 | A1 * | 7/2013 | McPeck | A61B 5/4839 600/383 |
| 2013/0303874 | A1 | 11/2013 | Diamond et al. | |
| 2014/0257073 | A1 | 9/2014 | Machon et al. | |
| 2015/0011857 | A1 * | 1/2015 | Henson | A61B 5/6831 600/383 |
| 2015/0025767 | A1 | 1/2015 | Feigel | |
| 2015/0257674 | A1 * | 9/2015 | Jordan | A61B 5/0006 600/383 |
| 2015/0313496 | A1 | 11/2015 | Connor | |

OTHER PUBLICATIONS

International Search Report, App. No. PCT/US2015/034841, dated Sep. 15, 2015.
International Preliminary Report on Patentability in International Application No. PCT/US2016/061853, dated May 15, 2018, 13 pages.

* cited by examiner

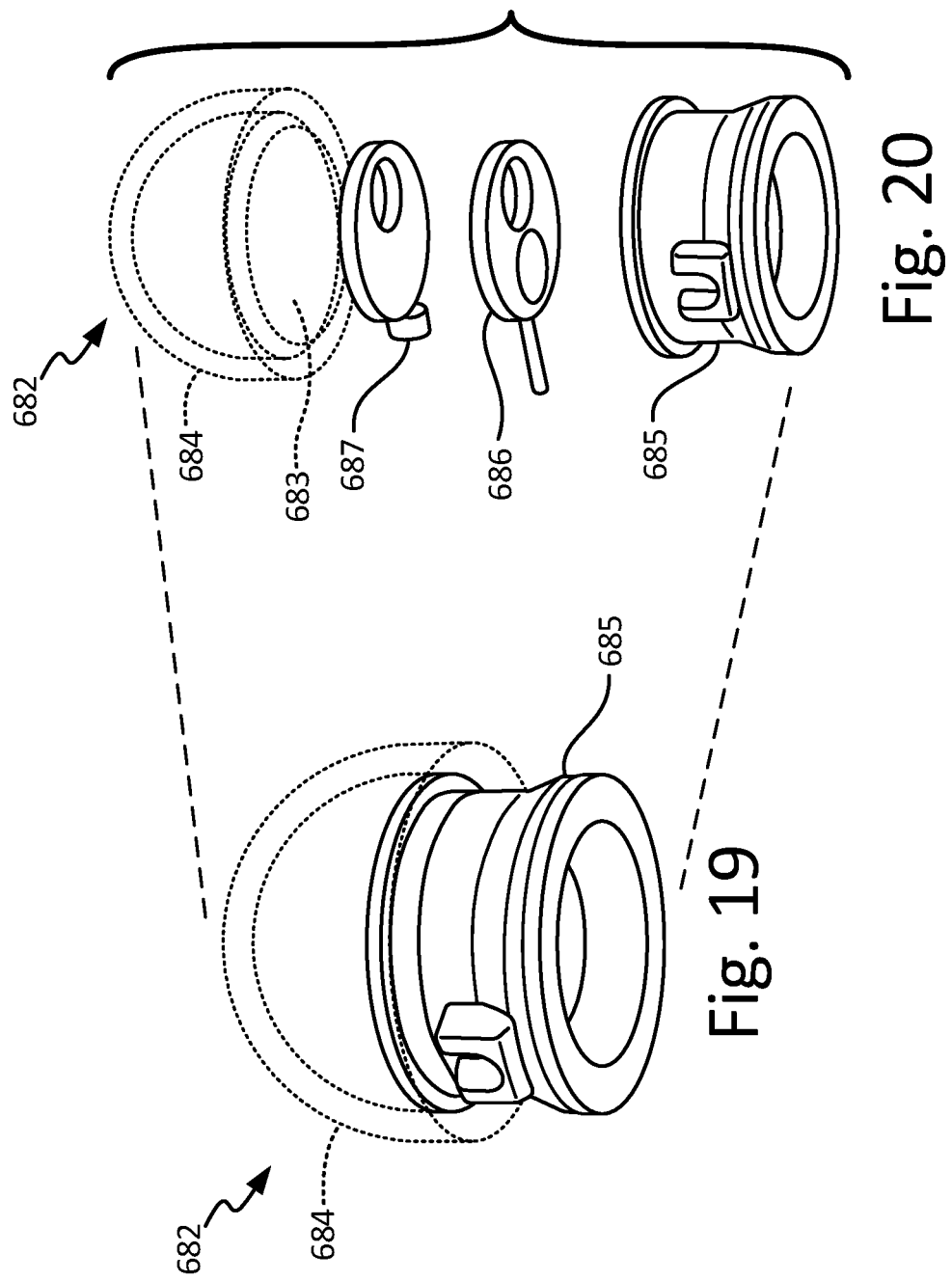

EEG HEADSETS WITH PRECISE AND CONSISTENT ELECTRODE POSITIONING

CROSS REFERENCE TO RELATED APPLICATIONS

This application claims the benefit of U.S. Provisional Application No. 62/255,238, filed Nov. 13, 2015. The disclosure of the prior application is considered part of and is incorporated in its entirety by reference in the disclosure of this application.

BACKGROUND

Electroencephalography ("EEG") headsets are used to acquire brain signal information from the surface of a subject's head adjacent the brain. EEG headsets have many applications, and the number of applications are expanding significantly. For example, EEG headsets have long been used in medical applications, and have typically been used in a medical facility where they are applied to the subject by trained medical personnel. One very common example of an EEG headset used in medical applications is a standard EEG skullcap, which includes a cap made of a rubber or rubber-like material that is put on the subject's head like a swimming cap, and the cap has numerous surface electrodes positioned throughout the cap in a manner such that they come in contact with surface of the subject's head. EEG headset designs like the standard EEG skullcap that cover the entire head have general applicability, and so can be used for many different applications. One downside however to such EEG headsets, and with current EEG headset designs in general, is that they are difficult for subjects to put on by themselves, and do so consistently so that electrodes are positioned in the same place in multiple different uses with the same subject.

One particular application area for EEG headsets is an area referred to as brain computer interface (BCI) or brain machine interface (BMI) applications. In a BCI or BMI system, brain signals are acquired from either an implanted or surface EEG electrode assembly, and processed in a computing system that ascertains the intent of the subject. Generally, the use of a BCI system includes a screening or learning mode in which the BCI system learns the brain signals a subject produces when thinking about or performing some specific thing, followed by an operation or chronic mode in which the BCI system continuously monitors brain signal information obtained using the electrode assembly to detect the presence of the learned brain signals, thus informing the BCI system of the subject's intentions. In the context of such a BCI system when using non-implanted electrodes like an EEG headset, ensuring that the electrodes are placed in the same position every time the system is used, including for example in multiple sessions of operational use, is challenging with existing EEG headset technology. In addition, there are other areas beyond BCI systems where electrode placement during multiple different sessions is important. Examples are chronic pain applications.

It is also known that different regions of the brain and frequencies of brain signals relate to different body functions, some examples of which are planning functions and motor control functions. For example, the brain signals acquired in a BCI system may be a specific type or frequency of brain signal acquired from a specific location of the brain, depending on what the BCI system is designed to do. One example of this location-specific nature of some BCI applications is the use of a BCI system for stroke patient rehabilitation, as described for example in U.S. patent application Ser. No. 12/133,919 to Leuthardt et al. and U.S. patent application Ser. No. 13/842,749 to Leuthardt et al. (the "Leuthardt et al. patent applications"), the disclosures of which are incorporated herein in their entireties. These patent applications describe, among other things, BCI systems to assist hemiparetic subjects, or in other words, subjects who have suffered a unilateral stroke brain insult and thus have an injury in, or mainly in, one hemisphere of the brain. For such patients, the other hemisphere of the brain may be uninjured and operating normally. The Leuthardt et al. patent applications describe an idea of ipsilateral control, in which brain signals from one side of the brain are used to control body functions on the same side of the body.

The location of the brain at which ipsilateral signals are produced is generally known, namely, a hand area of the motor and/or pre-motor cortex. That said, the position for any particular patient may be a little different from patient to patient, and therefore the location where an electrode needs to be positioned to detect the ipsilateral signal needs to be ascertained during a patient screening process for the patient. Once that location is identified and known, assuming that is possible, it is challenging using current EEG headset technology to consistently place electrodes of the EEG headset at the desired location to obtain the ipsilateral signal during multiple sessions in which the BCI system may be used. In addition, stroke patients may only have the use of one arm and hand. In addition, it may be desired to have stroke therapy rehabilitation utilizing a BCI system to be performed outside of a rehabilitation clinic such that there may be no assistance available to the stroke patient in putting on the BCI system including the headset. That is challenging however, in view of current EEG headset designs being difficult for stroke patients to put on by themselves using only one arm and hand. Further, it would be challenging for such patient to put existing technology EEG headsets on in the same way and location for multiple therapy sessions so that the electrode positioning is consistent from one session to the next.

SUMMARY

This document discloses EEG headset designs that address shortcomings in prior art headsets and also provide headset solutions for new and useful applications utilizing EEG headsets. One such application is brain computer interface (BCI) applications, and more specifically, a BCI application for stroke therapy in which the headset is utilized to obtain ipsilateral brain signals. This document also discloses BCI devices and methods utilizing EEG headsets.

In one aspect, this document discloses an EEG headset for recording electrical activity of a subject's brain. The device includes an electrode assembly comprising one or more body surface electrodes each configured to acquire an electrical signal present on a surface of a subject's head, the electrical signal being indicative of electrical activity present within a portion of the subject's brain. The device also includes wearable electrode registration assembly adapted to mate with the electrode assembly and having a front head engagement portion configured to engage with a location of the subject's head associated with the nose. The wearable electrode registration assembly is configured such that, when worn, the location wherein the one or more body surface electrodes contacts the subject's head is generally fixed with respect to the location of the subject's nose.

In various implementations, the system may have one or more additional features. For example, the front head engagement portion may be shaped to engage against a particular portion of the subject's nasion. In that case, the front head engagement portion may include an inwardly curved saddle structure having a surface that is shaped complementary with the particular portion of the subject's nasion.

In some implementations, the wearable electrode registration assembly may include an anterior-to-posterior wearable structure configured to be worn over the top of the subject's head and extend from a top of the subject's head, down the subject's forehead, to the front head engagement portion. The anterior-to-posterior wearable structure may be further configured to extend from the top of the subject's head, down the back of the subject's head, to a back head engagement portion. The back head engagement portion may include an inwardly curved structure having a surface that is shaped complementary with a particular portion of the subject's inion.

In the EEG headset, the wearable electrode registration assembly may also include at least one side head engagement portion configured to engage with a location of the subject's head associated with at least one ear. In this case the wearable electrode registration assembly is configured such that, when worn, the location wherein the one or more body surface electrodes contacts the subject's head is further generally fixed with respect to the location of at least one ear of the subject. The at least one side head engagement portion may be an inwardly curved end structure configured to engage the root of the helix of the ear. The at least one side head engagement portion may include two side head engagement portions, one side head engagement portion for positional registration with each of the subject's two ears. The wearable electrode registration assembly may include a transverse wearable structure configured to be worn over the top of the subject's head and extend from a top of the subject's head and down at least one side of the subject's head to the at least one side head engagement portion. In this case, the transverse wearable structure may be configured to extend from the top of the subject's head down both sides of the subject's head, and comprises a first side head engagement portion for positional registration with a first ear of the subject and a second side head engagement portion for positional registration with a second ear of the subject.

The electrode assembly of the EEG headset may be configured to mate with the wearable electrode registration assembly in a predefined manner that maintains the positioning of the one or more body surface electrodes with respect to the wearable electrode registration assembly. The electrode assembly may also include an assembly of one centrally located electrode and a plurality of peripheral electrodes. The plurality of peripheral electrodes may include three or more electrodes.

In another aspect, this document discloses a method of configuring an EEG BCI system. The method includes performing a BCI screening process using an EEG headset with multiple electrodes. The BCI screening process including providing an instruction to the subject to perform a task. The method also includes acquiring EEG brain signals using the multiple electrodes at a time to acquire EEG brain signals generated that are responsive to the instruction provided to the subject. The method further includes evaluating the acquired EEG brain signals to identify an electrode location subset comprising one or more of the multiple electrode locations in which there occurred significant brain activity responsive to the instruction provided to the subject. In this regard, the electrode location subset may comprise a subset of electrode locations corresponding to locations used in the BCI screening process, or one or more interpolated locations between the electrode locations of the BCI screening process. The method further comprises producing a custom EEG headset for the subject. The custom EEG headset comprises one or more electrodes configured to be positioned, when the EEG headset is worn by the subject, in a location of the subject's head associated with the identified electrode location subset.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 19 is a perspective view of another example electrode in accordance with some embodiments.

FIG. 20 is an exploded perspective view of the electrode of FIG. 19.

Like reference symbols in the various drawings, if utilized, indicate like elements.

DETAILED DESCRIPTION

Generally, this document discloses various designs of EEG headsets that overcome limitations of prior headset designs, and open the door to more new applications that require improved EEG headset designs. Generally, the EEG headsets disclosed in this document include three main components. First, the EEG headsets include a wearable electrode registration assembly, which serves to anchor or register the positioning of electrodes with respect to the head anatomy of the subject. Second, the EEG headsets include an electrode assembly adapted to mate with the wearable electrode registration assembly so that the electrode assembly is in a fixed position with the wearable electrode registration assembly. Third, the EEG headset includes circuit components necessary for a fully functioning EEG headset system including wireless transmission of brain signal information, including signal processing, battery power, and wireless transmission components.

Regarding the wearable electrode registration assembly specifically, the EEG headsets described herein include a nasion and inion registration component that engages the subject's nasion in the front of the subject's head and engages the inion at the back of subject's head, thus forming an anterior-to-posterior, or front-to-back, head wearable structure. The EEG headset designs disclosed herein can also include an ear registration component made up of a transverse or lateral component, and engaged to a particular location on each side of the head related to the subject's ear, for example, resting a top of the root of the helix of the subject's ear. The EEG headsets feature a fixed positioning of the electrode registration assembly with the wearable electrode registration assembly.

At a general level, some of the concepts implemented in the EEG headset designs include the following. First, the nose specifically (and nasion in particular), the nose and back of the head or inion, and the nose, inion, and ears may all be used as anatomical anchors for proper and consistent positioning of EEG electrodes at a particular position on the subject's head. The EEG headset designs are particularly well suited for small, location-specific brain signal collection, for example, the collection of ipsilateral brain signals, for example in the context of stroke therapy BCI applications. In addition, the EEG headset designs disclosed in this document provide not only consistency in electrode positioning, but also precision in positioning, especially for patients with degraded motor abilities who have to put the EEG headsets on for a therapy session.

EEG Headset Embodiment 1

Figure 3:
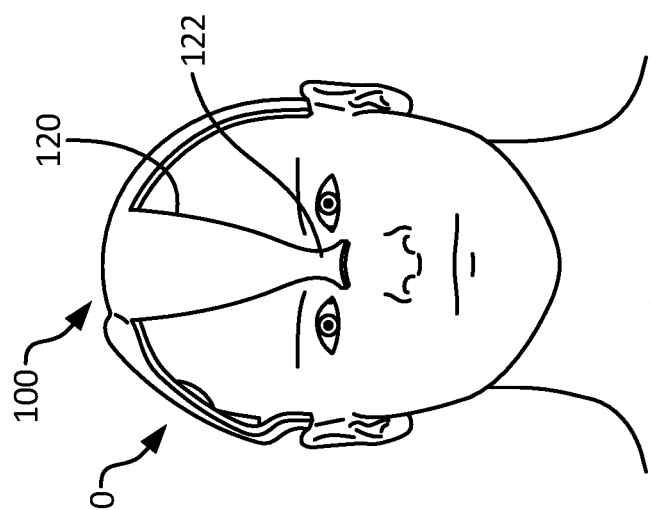
FIG. 3 is a front view of the EEG headset of FIG. 1.
Figure 2:
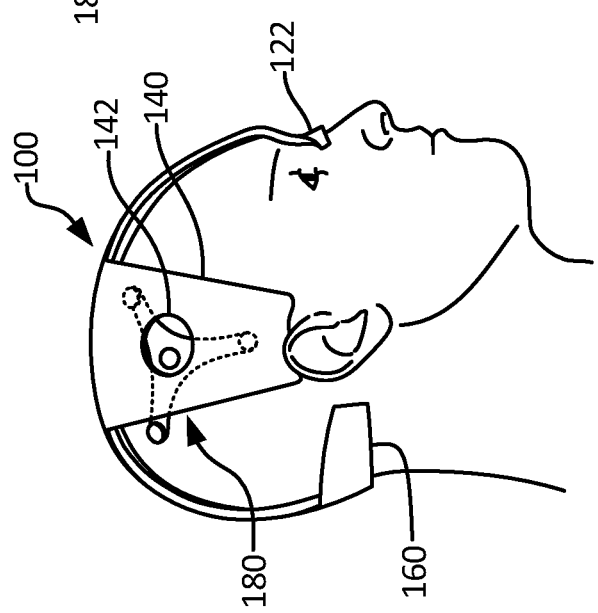
FIG. 2 is a right side view of the EEG headset of FIG. 1.
Figure 1:
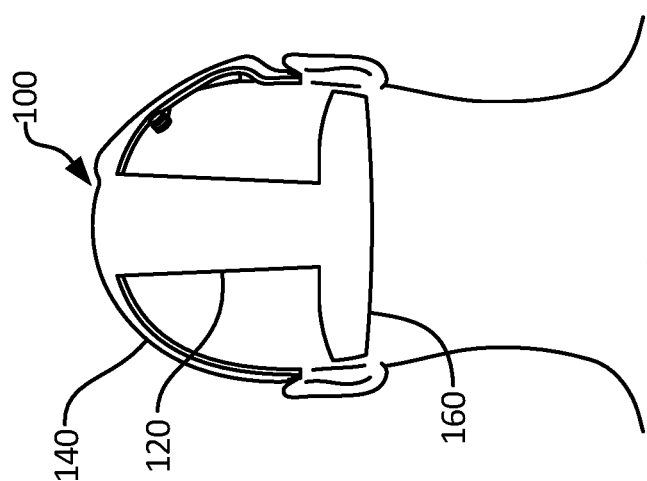
FIG. 1 is a rear view of a first example EEG headset in accordance with some embodiments.

Referring to FIGS. 1-3, in a first embodiment of an EEG headset 100, the EEG headset 100 utilizes a number of deformable thermoplastic strips, in this example three strips 120, 140, and 160. The fact that the three strips 120, 140, and 160 are made of a deformable material provides the ability to create a custom headset 100 on site for a particular patient. In this example embodiment, the strips 120, 140, and 160 are made of a low temperature thermoplastic material such as ethylene vinyl acetate (EVA), which may be heated to conform to the shape of an individual subject's head anatomy. Other deformable materials may be utilized. The construction of the headset 100 from the deformable strips 120, 140, and 160 will be described below, after a description of the components of the system.

In the depicted embodiment of headset 100, the three strips of thermoplastic material includes an anterior-to-posterior thermoplastic strip 120, a transverse or lateral thermoplastic strip 140 that when applied perpendicularly crosses the anterior-to-posterior strip 130 at the top of the subject's head, and finally, a back head engagement strip 160 that is attached at the back of the anterior-to-posterior strip 130 and extends transversely in the shape of a letter T in engagement with the subject's inion at the back of the neck.

Regarding the anterior-to-posterior thermoplastic strip 120 specifically, that strip 120 includes a front head engagement portion 122 shaped to engage the subject's nasion. Because the strip 120 is made of a thermoplastic material, the strip 120 can be deformed and tailored to the individual. The back head engagement portion 160 is shaped to engage the patient's inion, and may be in the form of a separate inion transverse strip 160 as shown for this embodiment. The transverse strip 160 in back may need to be deformed, tailored, and/or welded upon, given the anatomy of the particular patient. Different people have different anatomies, and the nature of the design herein can accommodate that. In this manner, the anterior-to-posterior strip 120 is anchored on the front side to the subject's nasion, and at the backside to the subject's inion. As such, the anterior-to-posterior strip 120 is anchored and the engagement at the front and the back prevent the strip 120 from moving laterally to either side.

Regarding the lateral or transverse thermoplastic strip 140 that provides an anchoring in relation to the subject's ears, the side head engagement portions as shown above are shaped to engage the subject's ear, resting upon the root of the ear's helix. In that manner, the ends of the transverse strip 140 are anchored to the ears so each end does not move forward or backward (that is, side to side from a perspective of viewing the ear). In alterative implementations, the saddle structure of the ends of the transverse strip 140 that engages the root of the ear helix may be more of a saddle (i.e., more concave or otherwise contoured) than what is shown. In other embodiments the strip 140 may loop around the ear, or be connectable to a strap that loops around the ear, and also may attach together under the chin. Having a chin strap may be useful in some embodiments to ensure that the electrodes are held sufficiently firmly in engagement with the subject's head so that an EEG signal may be acquired by the electrode. In some implementations, the technique of anchoring in relation to the subject's ears can additionally, or alternatively, include the use of a component member that engages into or at the ostium of the subject's ear canal(s) to facilitate a positive and secure location technique. It should be noted that in FIG. 3, the amount of protrusion from the surface of the head on each side is not symmetric, which is because the electrode assembly 180 is positioned under the transverse strip 140 on the right side of the subject's head in the depicted embodiment. In the depicted embodiment, there is shown an opening 142 in the transverse strip 140. This opening 142 allows for the electrode assembly 180 to be adjusted to the position that is identified during the subject's pre-screen as having the best signal quality. Such a position is patient specific. The electrode assembly 180 will be subsequently locked into this position, customizing the EEG headset 100 to the patient.

Figure 4:
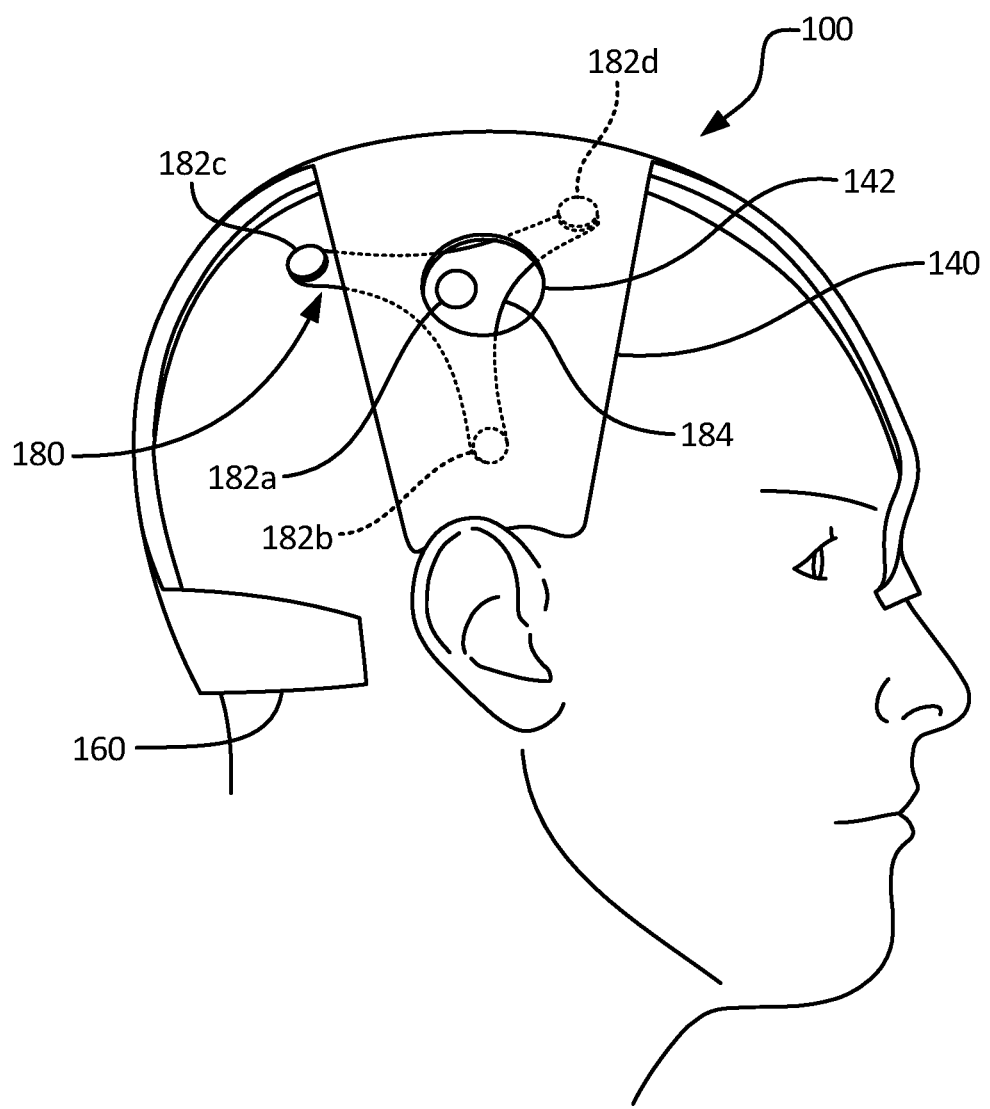
FIG. 4 is an enlarged view of a portion of FIG. 2.

Referring also to FIG. 4, the depicted embodiment of EEG headset 100 includes an electrode assembly 180 of four skin or surface electrodes 182a, 182b, 182c, and 182d. In this embodiment, the electrode assembly 180 is generally in the shape of a three-pointed star. In some embodiments, the electrode assembly 180 can include more or fewer electrodes than the arrangement of four electrodes 182a-d. For example, in some embodiments the electrode assembly 180 includes five electrodes (e.g., with one electrode in the center and four surrounding the center electrode). The electrode assembly 180, as shown, is positioned under the transverse strip 140 in a fixed position vis-à-vis the wearable registration assembly. The electrode assembly 180 includes an electrode support structure 184 which is in the shape of a three-pointed star, and includes four electrodes 182a-d that are each formed into or joined to the support structure 184. Connection wires (not shown) extend within the support structure 184 and connect to the electrodes 182a-d on one end, and at an opposite end to a connection structure (e.g., ribbon cable), which in turn may be connected to an electronics box including for example a battery and wireless transmitter circuitry. Such an electronics box may be provided at the back of the headset 100, for example coupled to the posterior portion of the anterior-to-posterior thermoplastic strip 120.

The layout of the four electrodes 182a-d in the depicted electrode assembly 180 includes a central electrode 182a and a plurality of peripheral electrodes (which in the example is three peripheral electrodes 182b-d). In a use wherein the EEG headset 100 is used to obtain an ipsilateral brain signal as shown in the depicted implementation, the central electrode 182a may be used to collect the ipsilateral brain signal, and the peripheral electrodes 182b-d may be used to collect signals from which to determine common mode noise, so that the common mode noise may be subtracted from the signal collected from the central electrode 182a. By way of example, one source of common mode noise may emanate from 60 Hertz lights. In some implementations, the EEG headset 100 could do the averaging and subtraction itself, and wirelessly transmit a brain signal obtained, for example, from the central electrode 182a with the common noise filtered out. Alternatively, the EEG headset 100 could transmit all four channels (one from each of the four electrodes 182a-d), and the processing to filter common mode noise may be performed in a separate component of the BCI system. The electrodes 182a-d may be wet or dry electrodes and may be active or passive electrodes, as will be explained below in connection with the circuit diagrams.

The electrode assembly 180 may be mated with the wearable registration assembly (e.g., with transverse strip 140) in a selectively fixed manner, which may be accomplished in a variety of ways. For example, the electrode assembly 180 and a corresponding thermoplastic strip 120, 140, and/or 160 may be fixedly mated by fixation means such as a screw or the electrode assembly 180 may be glued to the thermoplastic strip, to name but a few examples of how the two components may be fixedly mated with one another. The electrode cluster 180 can be positioned into the desired position (e.g., as dictated by the pre-scan). For example, in some implementations a clinician can move the electrode cluster 180 within the hole 142 in the headset 100 until it is in the desired position for each individual patient. Then the electrode assembly 180 can be locked in place (e.g., mechanically or chemically).

Figure 5:
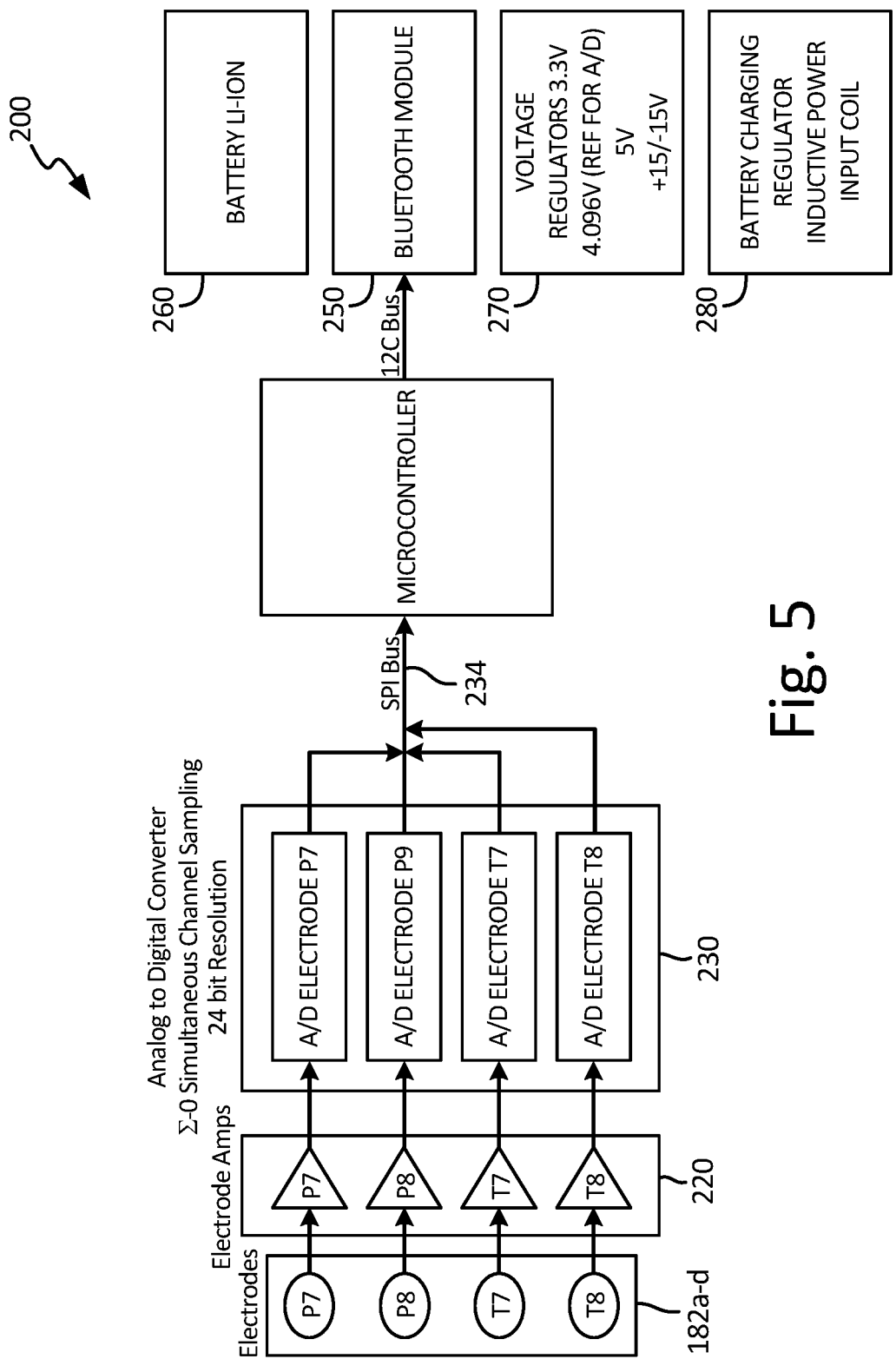
FIG. 5 is a schematic diagram of example electronics that can be used in conjunction with the EEG headsets described herein.

As mentioned, the EEG headset 100 may include an electronics box (not shown in FIGS. 1-4) located at the back of the EEG headset 100. Preferably, the positioning of the electronics box is such that it is located away from the recorded site, which as mentioned may be located at the back of the EEG headset 100, although different positions for the electronics box are also contemplated. One example of the electronics 200 for the EEG headset 100 is schematically depicted in FIG. 5.

As shown, the electronics 200 includes amplifier circuitry 220 to amplify the signal recorded at the electrodes 182a-d, and analog-to-digital (A/D) converter circuitry 230 to digitize the amplified sensed analog signal. The electronics 200 also includes controller circuitry (a microcontroller as shown) 240 which provides the glue logic between the A/D output and wireless transmitter circuitry 250, packaging up the data received from the A/D conversion circuitry 230, providing that packaged data to the wireless transmitter circuitry or module (which in this example is a Bluetooth module) 250, and controlling the wireless transmitter circuitry. The packaging of data includes assembling the A/D output into a format for a data transmission or messaging protocol, which in the example above is a Bluetooth protocol. The electronics also includes a battery or power source 260, voltage regulators 270, and a battery charging regulator 280. A power source such as the battery 260 shown is needed for the transmitter 250, microcontroller 240 and other circuitry, as well as the circuitry provided at the left side of FIG. 5. One example of a battery would be something similar to a cell phone battery, but other battery power sources may be applicable.

In terms of the location of the circuitry 200 in the headset system 100, the headset system 100 may include, as mentioned above, a battery/transmitter box which would be located away from the recording/electrode sites, for example, at the back of the headset attached to the back of the anterior-to-posterior thermoplastic strip 120, and a circuit board associated and located with the electrode assembly 180 remote from the battery/transmitter box and connected thereto with some connection structure such as a ribbon cable. The initial amplification circuitry 220 and A/D conversion circuitry 230 may be provided with the electrode assembly 180 (e.g., the star-shaped structure 184 with the electrodes 182a-d), and specifically on a circuit board provided with that electrode assembly 180 which may be, for example, on top of the electrodes 182a-d. In one embodiment, the battery/transmitter box includes all of the components shown in the right of FIG. 5, namely, the microcontroller 240, the battery 260, transmission (Bluetooth) module 250, and regulator circuitry 270 and 280. Alternatively, the microcontroller 240 may be provided with the electrode assembly 180, and not in the battery/transmitter box. In the embodiment shown in FIG. 5, there is provided a serial peripheral interface (SPI) 234 from the output of the A/D converter 230, to multiplex the digitized data onto one serial channel. As is known, the bus connection may include more than one line, for example to provide a chip select function. In other words, in this embodiment the interconnection does not require a separate wire for each channel. In addition, the A/D conversion circuitry 230 may be a multi-channel A/D converter which does not provide separate output channels anyway, so it would not matter. In addition to the circuitry 200, there may be provided an on/off switch for the user to activate, along with a light provided at the front of the headset 100 (which the user may see for example in a mirror) enabling the user to confirm that the headset power is activated or not.

The four electrodes 182a-d provided with the electrode assembly 180 may be wet electrodes or dry electrodes. For wet electrodes, a conductive gel may be utilized. The conductive gel provides an effective interface between the head and electrode, and prevents problems with the subject moving around, which may be the case in many use scenarios for the headset, for example, stroke therapy applications utilizing a BCI system. In effect, the wet electrode utilizing the EEG gel provides some cushion, and thus if electrode moves up and down the electrical contact will not break. With dry electrodes, care needs to be taken to possible issues regarding the fact that contact with skin may break momentarily, which may present problems in some use scenarios, although that may not occur or may not be a problem in other use scenarios.

The electrodes of the electrode assembly may operate in a passive mode or in an active mode. Operation in an active mode means some circuitry, typically an amplifier, is co-located with the electrode, with power provided to that amplifier circuitry, so that a signal is provided on a transmission line that is less vulnerable to noise. The sooner you amplify the sensed signal, there will be produced a low impedance path that may negate most noise sources. In a passive mode, the sensor sends a relatively weak electrical signal over a transmission line. To the extent the system may be able to be designed to operate in a passive mode and not have noise interfere with the system operation, doing so may be desirable for cost reasons. Passive electrodes are typically less expensive to fabricate or purchase (for example, perhaps one tenth the cost), and using a passive electrode design may provide more flexibility in the design in that electronics provided in a co-located fashion with the electrode would not be necessary. In addition, system design may be more difficult with an active mode operation because suppliers of active electrode component may not inform as to what the amplification characteristics may be, because that information may not be important in most applications, although it may be important in BCI applications, particularly if low intensity brain signals like an ipsilateral signal is being acquired and used.

Method of On-Site Fabrication of Embodiment 1 EEG Headset

Now will be described a method of making a customized EEG headset using deformable strip materials, such as thermoplastic strip materials. In the example described here, the application of the EEG headset is for a BCI system for stroke therapy utilizing the subject's ipsilateral brain signals, which is what the embodiment of the EEG headset 100 above is particularly well suited for given the position of the electrode assembly 180 corresponding to a location where ipsilateral brain signals may be sensed. In some cases, the brain signals to be used in stroke therapy may be contralateral brain signals, in addition to or as opposed to ipsilateral brain signals. Despite there being a specific application of the disclosed devices and methods below, it will be understood that the applicability of the devices and methods go beyond the use of ipsilateral signals and stroke therapy utilizing the subject's ipsilateral signals.

The first step of the method may be a BCI screening step in which the subject wears a standard EEG headcap with numerous electrodes all over the surface of the head adjacent the brain. With the EEG headcap on, the subject is instructed to perform particular functions such as thinking about or attempting to move an arm or hand. At an appropriate time following that instruction, the brain signals that the user produces are recorded and analyzed, and from that ipsilateral signals (i.e., brain signals located on the side of the brain that is on the same side of the body as the arm or hand that the subject was attempting or thinking about moving) may be identified (or in some cases, contralateral signals or a combination of ipsilateral and contralateral signals), specifically identifying the electrode location where the signals were acquired and the frequencies and timing of those ipsilateral brain signals. More generally, a "hot spot" area of brain activity responsive to the instruction provided to the subject is identified, or in other words, the precise location (s) of the electrodes is/are identified in which there occurred the most informative brain activity about the subject's behavior produced in response to the instruction.

After the location where the ipsilateral signals is identified (or more generally, the "hot spot" or precise locations of the electrodes is identified in which there occurred the most informative brain activity), the subject's scalp may be marked with a marker for example, thus physically identifying the location on the subject's head where ipsilateral signal or "hot spot" signals may be acquired. The location may be a single location or multiple locations. In addition, the location may correspond exactly to the location where an electrode of the standard EEG headset was located, or the location may be an interpolated location between two or more different locations where electrodes of the standard EEG headset were located. Then, the standard EEG headcap may be removed, and construction of the customized EEG headset begins.

Figure 6:
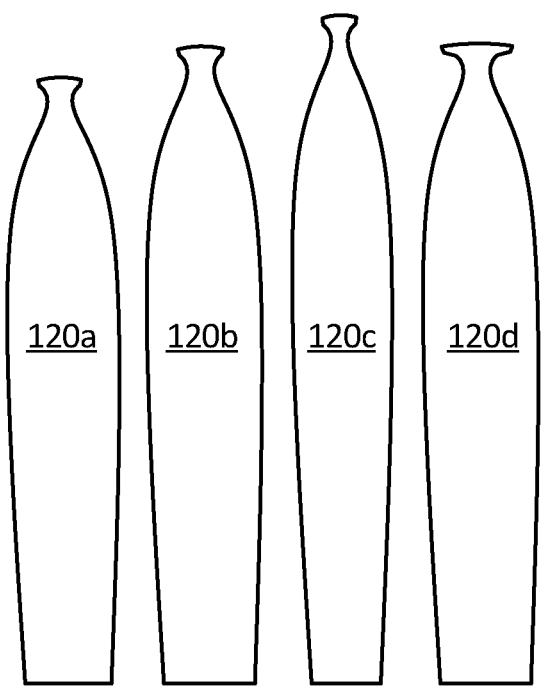
FIG. 6 is a top view of an assortment of deformable anterior-to-posterior thermoplastic strips that can be used to form some embodiments of the EEG headsets described herein.
Figures 7, 8:
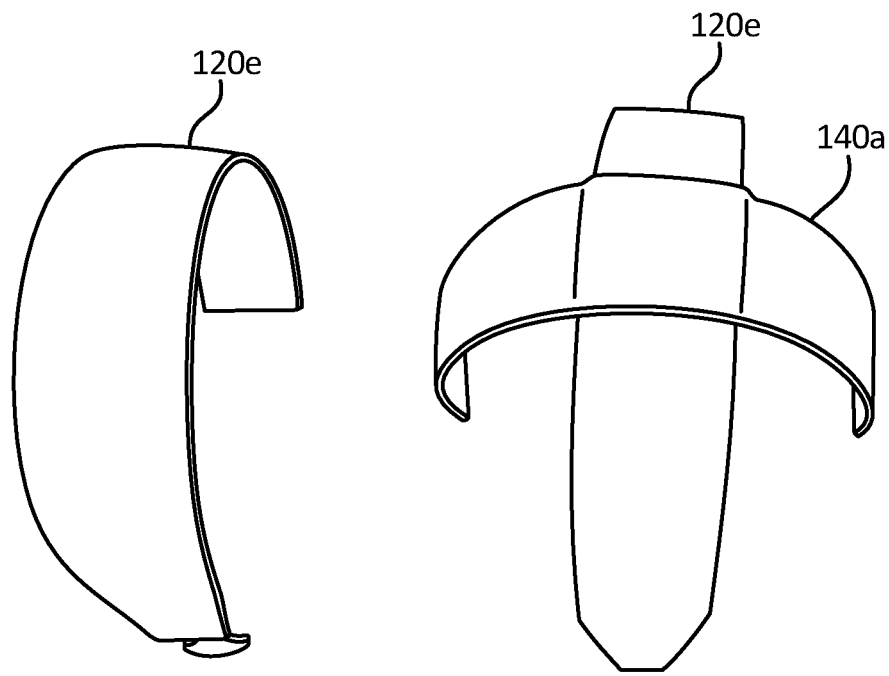
FIG. 7 is a top perspective view of a curved anterior-to-posterior thermoplastic strip.
FIG. 8 is a top perspective view of a curved anterior-to-posterior strip attached with a curved transverse strip.

FIGS. 6-8 illustrate the thermoplastic strip materials and steps involved in constructing a customized EEG headset. While the process described below involves "welding" pieces together, some embodiments may not require any "welding" by the technician to fit the headset to the patient. For example, in some embodiments, the headset incorporates a single unitary piece of thermoplastic that is manufactured by a die-cutting process from a larger sheet of material.

In some implementations, the first step in constructing the customized EEG headset is to start with three stock pieces of straight or moderately curved thermoplastic material. For example, FIG. 6 shows stock pieces 120*a*, 120*b*, 120*c*, and 120*d* for the anterior-to-posterior strip 120. Note that the strips have a T configuration on one end of the strip 120*a-d* (at the top in FIG. 6), which is the portion of the strip 120*a-d* that will be deformed for engagement with the subject's nasion. The anterior-to-posterior strip 120*a-d* before deformation may alternatively also include a longer T at the opposite end of the strip 120*a-d*, for engagement with the subject's inion, a bony ledge portion of at the back of the head. In the present embodiment, however, the transverse strip for engagement with the inion is a separate strip from the anterior-to-posterior strip 120*a-d* which becomes permanently affixed during the assembly process. In terms of the sizing of the strips, a number of different sizes may be provided to accommodate different sizes of heads. In addition, cutting and trimming of the strips may be performed to the extent a particular standard size of strip is not quite right for a particular patient. Alternatively, some implementations provide full (or near-full) head coverage with a single piece of the thermoplastic (like a helmet) rather than a series of strips. Another embodiment provides a headband-like shape. In some such embodiments, the thermoplastic is die-cut to a flat ring-shape. The ring is heated and then pressed over the patient's head (forming into a shape around the head that looks like a headband sitting just over the tops of the patient's ears).

Step two is to apply the anterior-to-posterior strip to the subject, deforming the strip appropriately to the shape of the subject's head in the process, as depicted in FIG. 7. This is done by first heating up the strip 120*e* to a specified temperature, typically with a heat gun or in a hot water bath at about 60° C. to 75° C., whereupon the strip 120*e* gets flexible and it can be put on someone's head and deformed to the shape of the head. It may be desirable or necessary to cool down the thermoplastic strip 120e somewhat, but not completely so that it is still deformable, before the strip 120e is applied to the person's head.

The third step, as depicted in FIG. 8, is to apply the transverse (lateral strip) 140a to the subject. This thermoplastic strip 140a may be formed in a similar way to the anterior-to-posterior strip 120e. In addition, in an application such as the one depicted in FIG. 1-4 where the electrode assembly 180 engages with the transverse strip 140, the electrode assembly 180 may be placed against the head before the transverse strip 140a is applied to the head, so that the transverse strip 140a not only conforms with the shape of the subject's head, but also conforms to the shape of the electrode assembly 180 provided under the transverse strip 140a. In addition, the heating of the transverse strip 140a and application of that strip over the anterior-to-posterior strip 120e at the top of the patient's head will cause the two strips to fuse or weld together. FIG. 8 shows perpendicularly crossed strips 120e and 140a fused together. Alternatively, some embodiments may not require any fusing or welding strips together to fit the headset to the patient. For example, in some embodiments, the headset includes a single unitary piece of thermoplastic that is manufactured by a die-cutting process from a larger sheet of material.

The fourth step is to apply a third strip (e.g., the inion transverse strip 160 as shown in FIG. 1-4) to engage with the subject's inion, at the back of the subject's head. This strip 160 would be formed similarly as the first two strips 120e and 140a, and would become fused with the anterior-to-posterior strip 120e at the back portion of that strip 120e, so that the anterior-to-posterior strip 120e and the inion transverse strip 160 form a T configuration, with the inion transverse strip 160 engaging with the inion and conforming in shape with the inion.

Next, in the fifth step, the electrode assembly (e.g., the electrode assembly 180) may be attached to the electrode registration assembly (that is, to the multiple configured strips) at a particular location of the electrode registration assembly so that the electrodes are provided to obtain the "hot spot" signals identified during screening, which in the examples above would be on the right side of the transverse strip 140/140a. In particular, as shown in FIGS. 1-4, the electrode assembly is attached underneath the transverse strip 140/140a. As also discussed in the third step above, the electrode assembly may also be positioned against the head while the transverse strip 140a is being deformed in the third step discussed above, so that the transverse strip 140a conforms not only to the head of the subject but also to the shape of the electrode assembly positioned under the transverse strip 140a. The attachment of the electrode assembly to the transverse strip 140a may be accomplished with the use of screws or glue or some other appropriate fixation mechanism, or alternatively a groove in the transverse strip 140a corresponding to the electrode assembly which groove is created when the strip 140a is deformed may be sufficient in terms of creating a fixed positioning between the strip 140a and the electrode assembly.

In the sixth step, a battery/transmitter box may be provided on the headset, for example attached to the back part of the anterior-to-posterior strip 120e. A ribbon cable for example may also be provided to interconnect the electrode assembly with the battery/transmitter box. Finally, in the seventh step, and on/off switch and corresponding light may be provided with the headset as discussed above, for example, at the front of the device so the subject is able to see in a mirror that it is on.

EEG Headset Embodiment 2A

Figure 10:
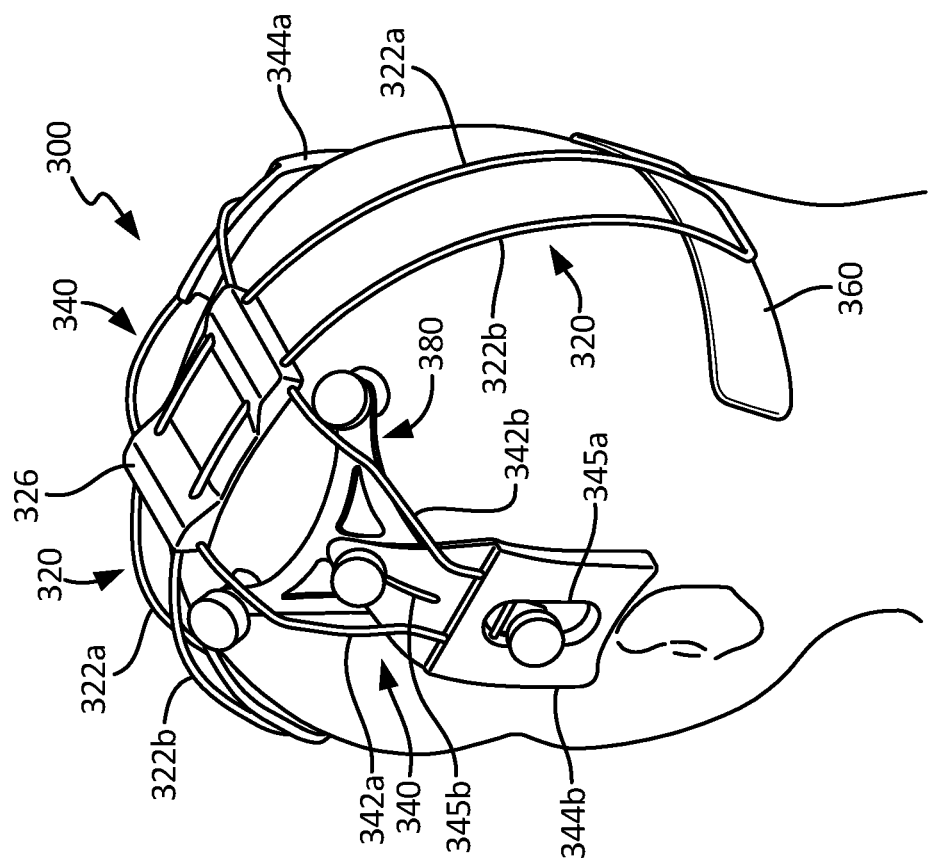
FIG. 10 is a rear perspective view of the EEG headset of FIG. 9.
Figure 9:
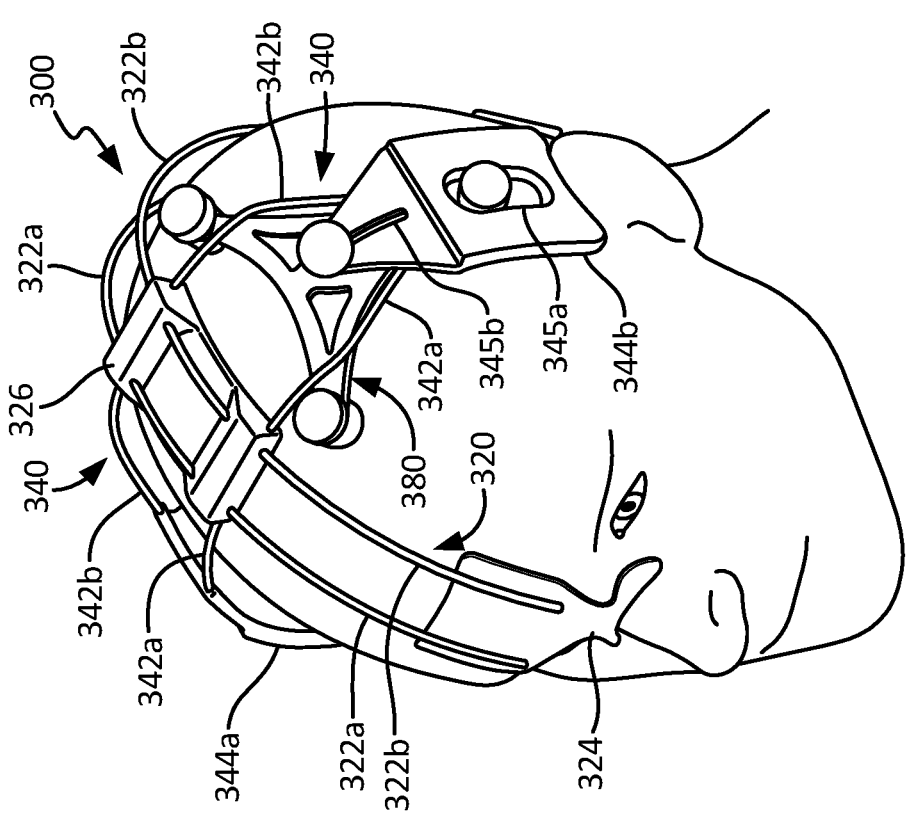
FIG. 9 is a front perspective view of another example EEG headset in accordance with some embodiments.
Figure 11:
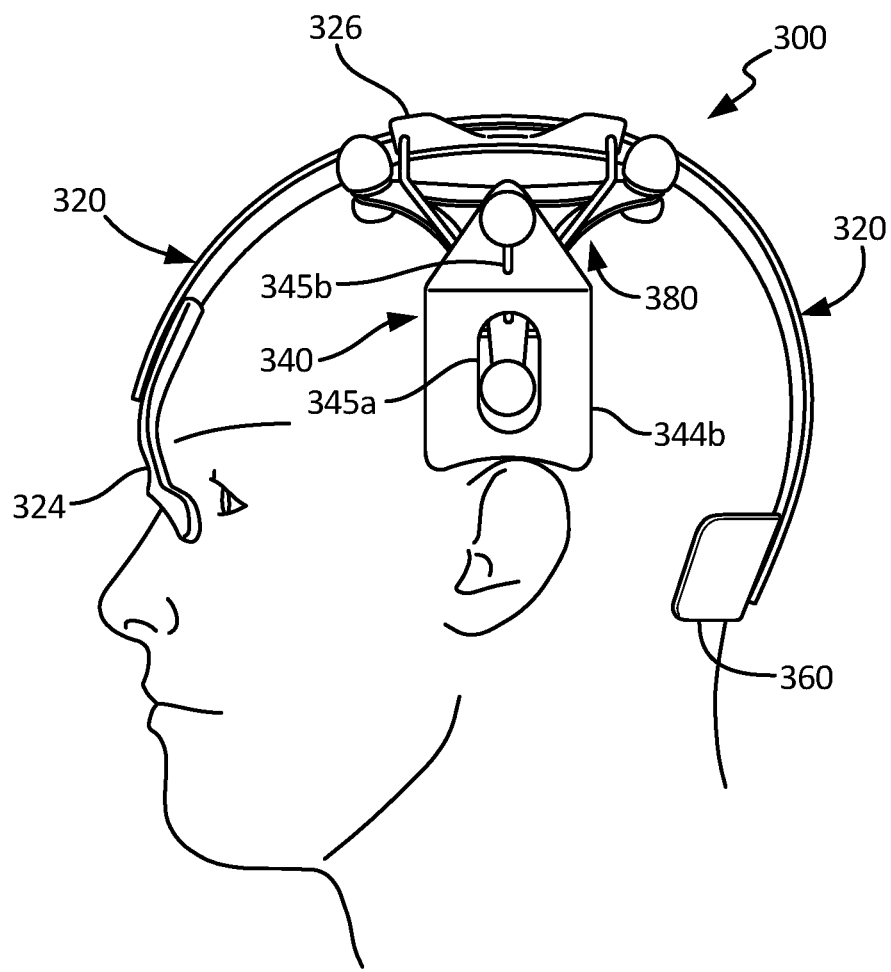
FIG. 11 is a left side view of the EEG headset of FIG. 9.

In a second general embodiment of a customized EEG headset 300, a wearable electrode registration assembly includes configurable wire frame structures and an electrode assembly 380 that is adjustable relative to the wearable electrode registration assembly, as shown in FIGS. 9-11. This embodiment will be referred to as Embodiment 2A, in that a variation of this wire framework design will be discussed below, and will be referred to as Embodiment 2B.

As shown, the wearable electrode registration assembly of the EEG headset 300 includes an anterior-to-posterior structure 320 engaging the nasion at the front of the head and the inion at the back of the head, and a transverse or lateral structure 340 engaging the root of the ear helix on both sides of the subject's head. Each of these two main structures 320 and 340 of the wearable electrode registration assembly include wire frame connecting components 322a-b and 342a-b, and head engagement components (as described below). The headset 300 also includes an electrode assembly 380, which in the configuration shown is positioned on the left side of the subject at a location to acquire ipsilateral brain signals from the left side of the subject's brain.

The electrode registration assembly of embodiment 2A shown above includes five head engagement components, namely, (1) a nasion engagement component 324, (2) a top-of-the-head engagement component 326, (3) an inion engagement component 360, and (4/5) two ear engagement components 344a and 344b that rest upon the top of the root of the ear's helix. These components may be fabricated using an injection molding process. Alternatively, one or more of the head engagement components may be fabricated using thermoplastic material so that they may be made to conform closely to the anatomy of the subject. Customization of some of the head engagement components is more important than with others. For example, the nasion engagement component 324 and the inion engagement component 360 structures may be required to conform closely to the anatomy of the subject. This may be accomplished for example by having a number of shapes and sizes of such head engagement structures in an inventory, and one is selected that conforms most closely to the anatomy of the subject. Alternatively, a scan of the subject's anatomy may be made, and the head engagement structures produced on site using three-dimensional or additive manufacturing techniques. Further yet, the nasion and inion engaging components 324 and 360 may be made of a thermoplastic material and deformed such that it conforms closely to the shape of the subject's nasion and inion. For head engagement components wherein customization to the particular patient is not that critical, for example, the ear engagement components 344a-b and the top of the head component 326, these components may be standard for all subjects.

The anterior-to-posterior structure 320 includes a wire frame structure which in this embodiment consists of two parallel elongate wires 322a and 322b, each of which is attached at one end to the nasion engagement structure 324, extends from there though the top-of-the-head engagement structure 326, and to the inion engagement structure 360 to which the two elongate wires 322a-b are attached. The elongate wires 322a-b of the anterior-to-posterior structure 320 may be configured to be slightly spaced away from the surface of the subject's head, as shown. The transverse structure 340 similarly includes a two-wire frame structure, which in this embodiment consists of two parallel elongate wires 342a and 342b, each of which is attached at one end to one ear engagement structure 344a/344b, extends from there through the top-of-the-head engagement structure 326, and to the other ear engagement structure 344a/344b to which the two elongate wires 342a-b are attached. The elongate wires 342a-b of the transverse structure 340 may similarly be configured to be slightly spaced away from the surface of the subject's head, as shown.

The top-of-the-head engagement structure 326 may be adjustable in relation to the wires 322a-b and 342a-b, in other words, the wires 322a-b and 342a-b are slideably provided within lumens passing through the top-of-the-head engagement structure 326. A mechanism may be included with the top-of-the-head engagement mechanism 326 so that the position of the wires 322a-b and 342a-b in the lumens is set by a structure clamping down on the wire passing through the lumen, and then released again so that the wires 322a-b and 342a-b the top-of-the-head engagement mechanism 326 may be slid over the wires to a different position. This enables adjustment of the position wherein the electrodes of the electrode assembly 380 contact the head, as will be discussed in more detail below.

The length of the wire engagement structures can be configured on site for a particular subject's head size. For example, in one embodiment, the wire framework 322a-b making up the anterior-to-posterior structure 320 may be provided to the site with the ends of the two wires 322a-b permanently affixed to the inion engagement structure 360. The opposite ends of these two wires 322a-b may be cut on site to an appropriate length, and then these ends of the wires 322a-b may be engaged to the nasion engagement structure 324 by suitable mechanism such as a snap fit. As such, the length of the anterior-to-posterior structure 320 may be customized for the particular structure on site. Similarly regarding the transverse structure 340, the wire framework 342a-b may be permanently affixed at one end to one of the ear engagement structures 344a/344b, and engagement to the opposite ear structure 344a/344b may be done on site by suitable engagement mechanism such as a snap fit, after the two wires 342a-b are cut to an appropriate length for the subject. As such, the length of the transverse structure 340 may similarly be customized for the particular structure on site.

The electrode assembly 380 comprises a four electrode structure with a central electrode and three peripheral electrodes, similar in design to the electrode assembly 180 of the first embodiment. Adjustability of the electrode positioning relative to the head is provided with this embodiment of the EEG headset 300 as follows. First, for the up and down adjustability, the ear engagement structure 344b in this embodiment is provided with a slot 345a located in a central portion of the ear engagement structure 344b and vertically oriented, within which central slot 345a one of the three peripheral electrode structures engages and can be adjusted up and down (up and down from a perspective of the headset as worn). The ear engagement structure also includes a second slot 345b located at an upper end portion of the ear engagement structure 344b and similarly vertically oriented parallel with the central slot 345a, within which upper end slot 345b the central electrode structure engages and can be adjusted up and down (up and down, again, from a perspective of the headset as worn). Accordingly, as shown in the figures above, the electrode assembly 380 may be adjusted relative to the ear engagement structure 344b so that the electrode assembly 380 is farther away or closer to that particular ear. To do so, an engagement and release mechanism may be provided with the ear engagement structure 344b, and when in a released position, the electrode assembly 380 may be moved up or down, whereupon the peripheral electrode in engagement with the central slot 345a moves up or down within the central slot 345a, and whereupon the central electrode in engagement with the upper end slot 345b moves up or down within the upper end slot 345b. When the electrode assembly 380 is put in a desired location, the engage/release mechanism may be engaged to lock the electrode structure 380 in that position. In addition to the electrode assembly 380 being adjustable so that it is located farther away from the ear, if necessary the top-of-the-head engagement structure 326 may be adjustably slid over the wires 342a-b away from the ear (namely, the left ear in the example depicted above) in the event that the desired location for the central electrode is farther away from the left ear and the top-of-the-head engagement 326 may otherwise impede the up adjustment of the electrode assembly 380.

Fore and aft adjustability of the electrode assembly 380 position relative to the head is also provided. To adjust fore and aft, movement of the top-of-the-head engagement structure 326 forward or backward over the parallel wires 322a-b of the anterior-to-posterior structure 320, moves the electrode structure 380 fore and aft, owing to the parallel wires 342a-b of the transverse structure 340 being also in engagement with the top-of-the-head engagement structure 326. As discussed above, an engagement and release mechanism may be provided to enable the movement of the top-of-the-head engagement structure 326 over the wires 322a-b forward or backward, and then when the desired location of the electrode assembly 380 in relation to the head is reached, the mechanism may be set to lock the position of the top-of-the-head engagement structure 326 in place with respect to the two parallel wires 322a-b.

Figure 12:
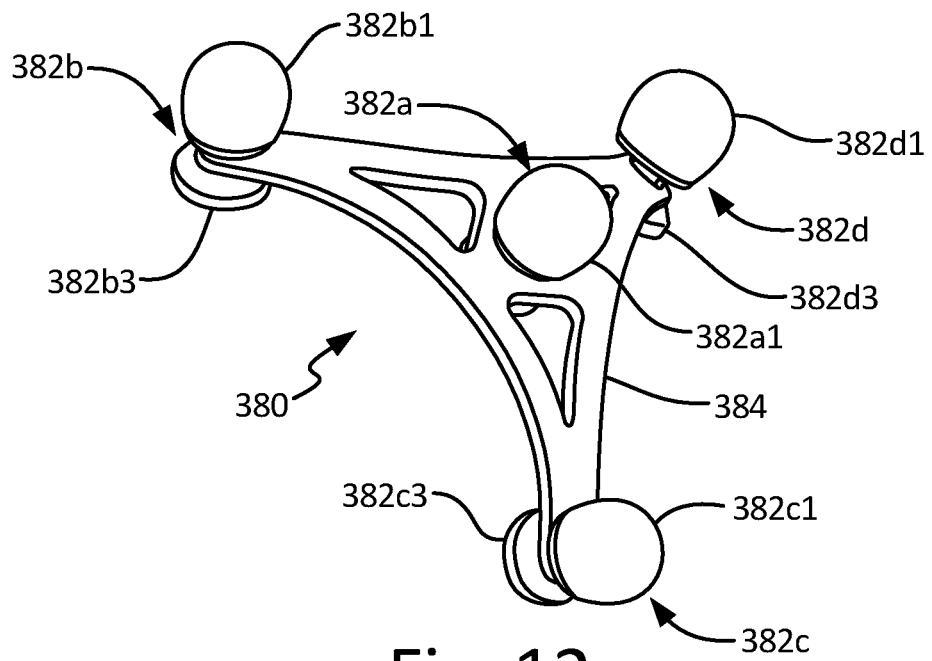
FIG. 12 is a perspective view of an electrode assembly of the EEG headset of FIG. 9.
Figure 13:
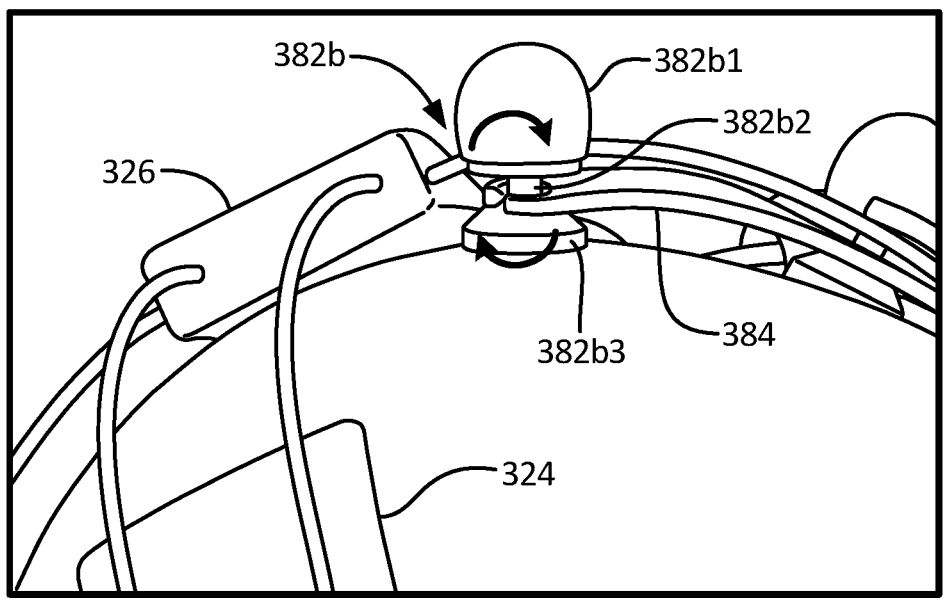
FIG. 13 is an enlarged view of a portion of the EEG headset of FIG. 9.

Further detail of the electrode assembly 380, which may be referred to as a "sensor puck," is provided in FIGS. 12 and 13. The electrode assembly 380 is provided on a support structure 384 in the shape of a triangle or three-pointed star, and has one central electrode 382a and three peripheral electrodes 382b-d to provide the functionality described above to obtain a brain signal using the central electrode 382a and use the peripheral electrodes 382b-d to eliminate common mode noise from the signal obtained by the central electrode 382a.

Each electrode 382a-d has a respective upper portion 382a1, 382b1, 382c1, and 382d1 that is located above the support structure 384, a respective middle waist portion (e.g., see representative middle waist portion 382b2 of electrode 382b in FIG. 13) that is in engagement with the support structure 384, and a respective lower portion 382a3, 382b3, 382c3, and 382d3 comprising the electrode that is placed in contact with the head. Gel reservoirs may be provided in each of the electrode structures 382a-d, for example in the upper portion 382a1, 382b1, 382c1, and 382d1 of the electrode structure 382a-d, so that gel may be provided to the electrode 382a3, 382b3, 382c3, and 382d3 to provide wet electrode engagement with the skin. The upper portion 382a1, 382b1, 382c1, and 382d1 of the electrode structure 382a-d in this embodiment has a bellows structure in which gel is provided, which bellows structure may be squeezed by a user to provide gel at the location of the electrode 382a3, 382b3, 382c3, and 382d3 so that the gel is provided between the electrode 382a3, 382b3, 382c3, and 382d3 and the surface of the subject's head. Each of the four electrode structures 382a-d may also include a circuit board that may include amplification circuitry for an active electrode configuration. Each of the four electrode structures 382a-d may also have freedom to pivot in relation to the support structure 384 so that the electrodes 382a3, 382b3, 382c3, and 382d3 make full contact with the surface of the subject's head.

Figure 14:
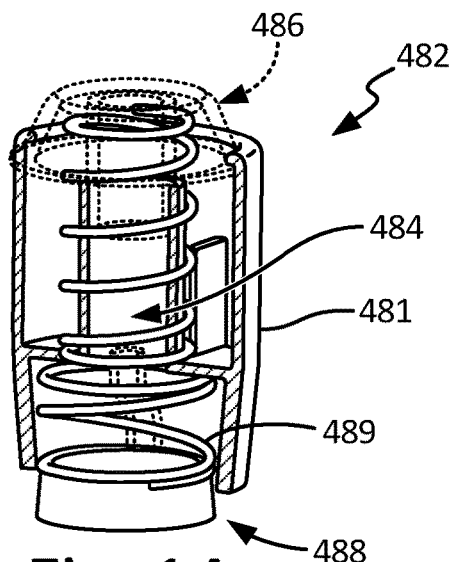
FIG. 14 is a partial cutaway view of an example electrode in accordance with some embodiments.
Figure 15:
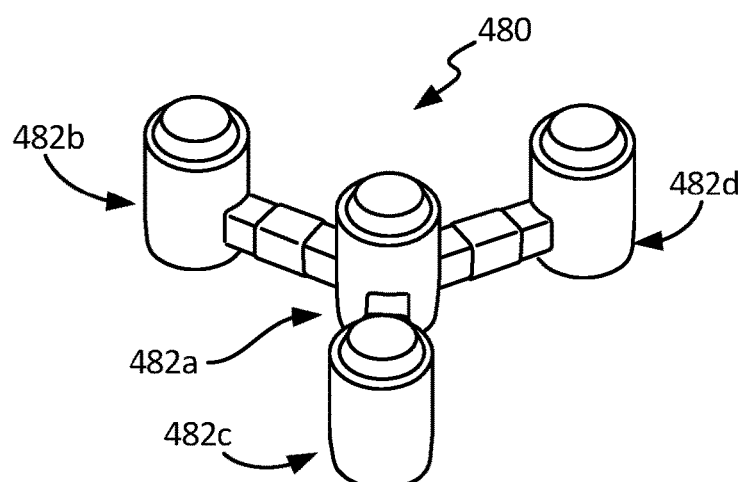
FIG. 15 is a top perspective view of an example electrode assembly including multiple electrodes like the electrode of FIG. 14.
Figure 16:
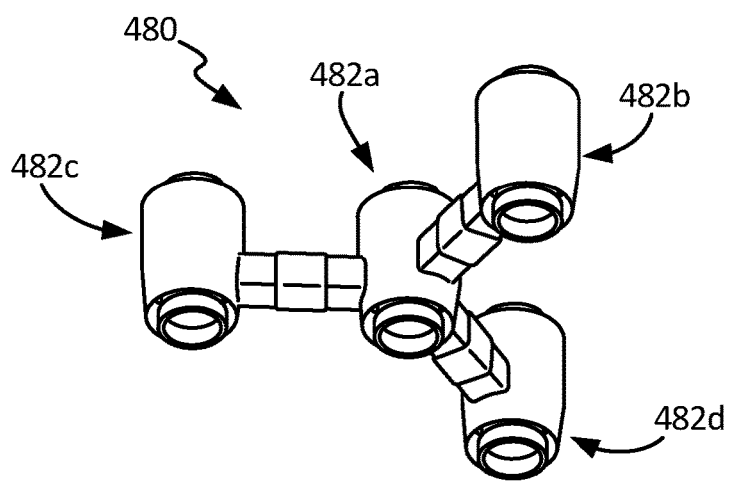
FIG. 16 is a bottom perspective view of the electrode assembly of FIG. 15.

To illustrate an example configuration of a gel reservoir provided with each electrode structure 382a-d, detail of an example electrode structure 482 is shown in FIG. 14 that is shown, in turn, in the context of an alternative embodiment for an electrode assembly 480 in FIGS. 15 and 16. The depicted implementation of the electrode assembly 480 also includes a central electrode structure 482a and three peripheral electrode structures 482b-d in a hub and spoke configuration. Each of the four electrode structures 482a-d of the assembly 480 of this embodiment may be constructed similarly (e.g., like electrode structure 482 shown in FIG. 14). In this embodiment, the electrode structure 482 includes a housing for a refillable or replaceable gel reservoir 484. Above the gel reservoir is a pumping mechanism 486 in engagement with the reservoir 484 to pump gel out of the reservoir to the electrode location 488. Tubing extends from the gel reservoir 484 to the location of the electrode 488, to transmit gel so that it is provided between the surface of electrode 488 and the subject's head. A spring 489 is provided that is engagement with the electrode structure 482 housing 481, upon which spring 489 the electrode 488 is mounted so that the electrode 488 "floats" for good cranial apposition. The spring mounting of the electrode 488 also provided controlled apposition force.

Figure 17:
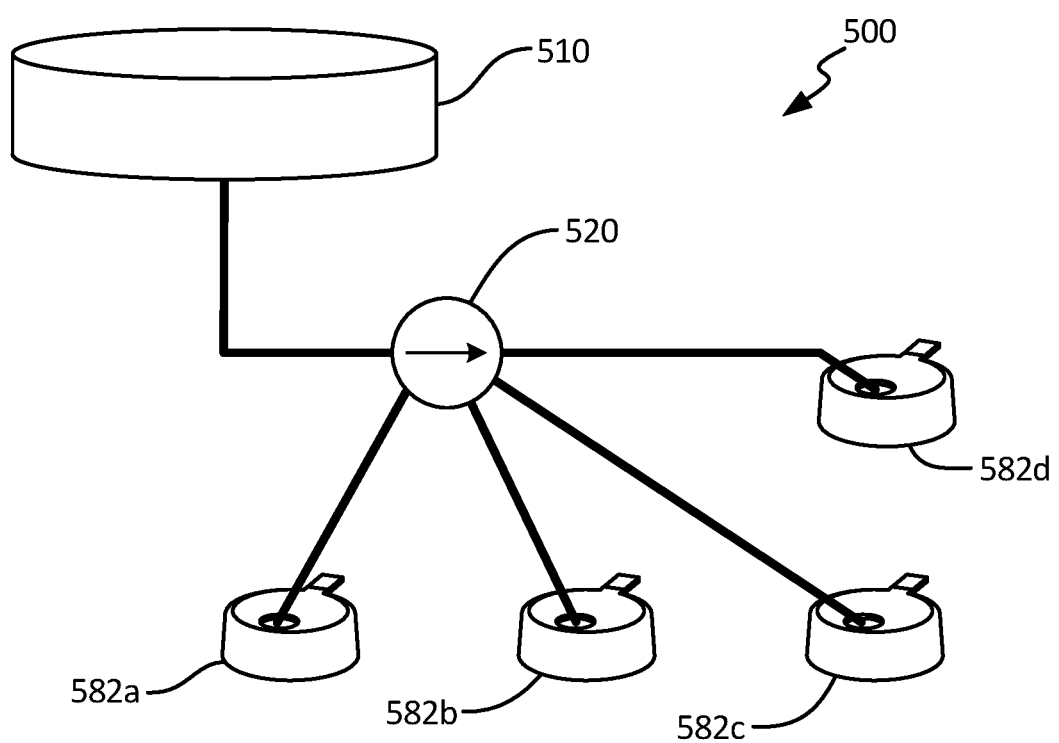
FIG. 17 is a schematic diagram of another electrode assembly in accordance with some embodiments.

In alternative embodiments, as schematically shown in FIG. 17, a common gel reservoir 510 may be provided for an entire electrode assembly 500, and may serve each of the multiple electrodes 582a-d on the electrode assembly 500.

The EEG gel delivery mechanism shown in FIG. 17 includes the common gel reservoir 510, and a user selectable multi-position valve 520 to deliver gel to each of the four electrodes 582a-d one at a time. Alternatively, the gel delivery mechanism of the electrode assembly 500 may be configured to deliver gel to all electrodes 582a-d at the same time.

EEG Headset Embodiment 2B

Figure 18:
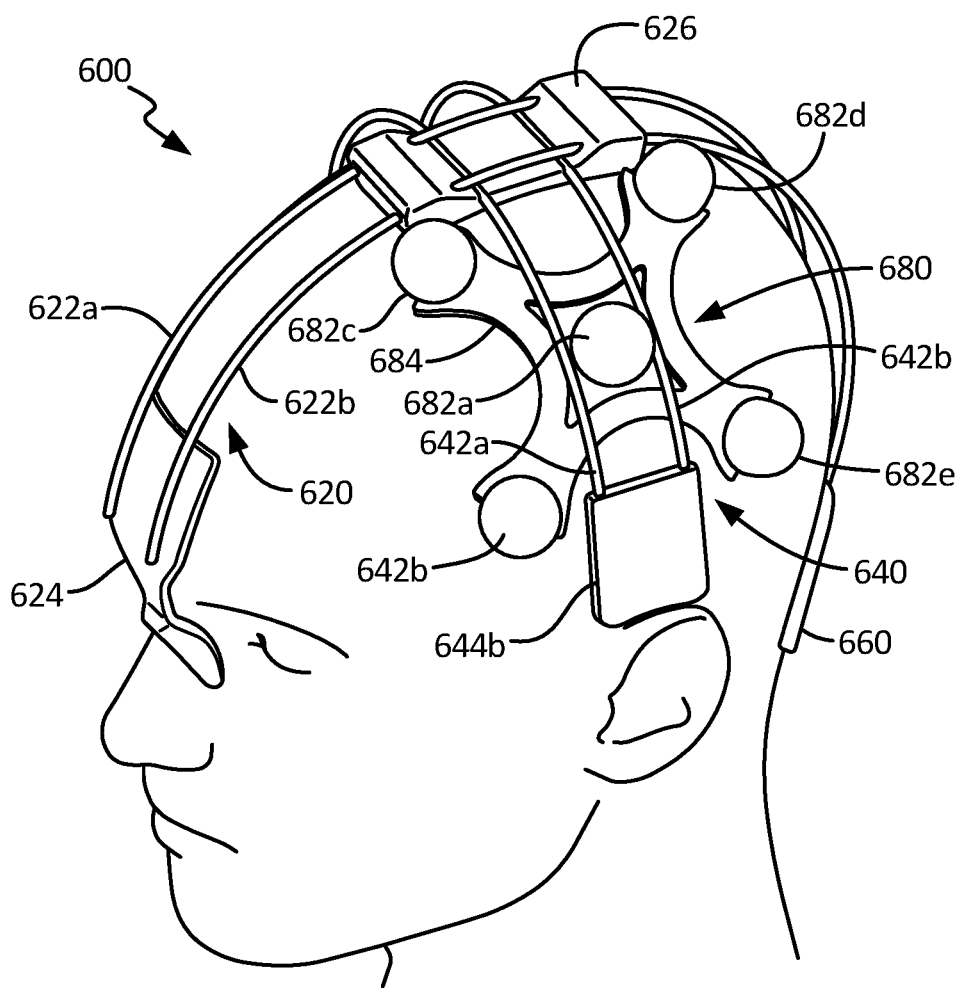
FIG. 18 is a front perspective view of another example EEG headset in accordance with some embodiments.

Embodiment 2B of an EEG headset 600 is a variation of Embodiment 2A, and is shown in FIG. 18. This embodiment is similar to embodiment 2A in that it has five head engagement structures, an anterior-to-posterior wire pair 622a-b extending from the nasion engagement structure 624 to the inion engagement structure 660, and a transverse wire pair 642a-b extending from one ear engagement structure 644a (not visible) to the other ear engagement structure 644b. In this embodiment, up and down adjustability of the electrode structure 680 in relation to the head is provided by the central electrode structure 684 sliding up and down within the transverse wire pair 642a-b, engaging a forward wire 642a on a front side of the electrode structure 680 and a rearward wire 642b on a rearward side of the electrode structure 680. Fore and aft movement of the electrode structure 680 in relation to the head is provided in embodiment 2B as it is in embodiment 2A, with the top-of-the-head engagement structure 626 being slid either forward or rearward over the anterior-to-posterior wire pair 622a-b. As with embodiment 2A, the forward or rearward movement of the top-of-the-head engagement structure 626 moves forward or rearward the attached transverse wire pair 642a-b, and thus the electrode assembly 680 mated with the transverse wire pair 642a-b.

The electrode assembly 680 of embodiment 2B includes a support structure 684 shaped as a four-pointed star, and five electrode structures 682a-e including one central electrode structure 682a and four peripheral electrode structures 682b-e. The electrode assembly support structure 684 and electrode structures 682a-e are configured so that the electrode structures 682a-e engage in a snap fit relationship. The design of the five electrode structures 682a-e is the same and is shown in more detail by example electrode structure 682 of FIGS. 19 and 20.

As shown, the electrode structure 682 includes a refillable EEG gel reservoir 683 defined within a low durometer, dome shaped bellows 684 with a dome on top and circular opening at the bottom of the bellows, the bellows comprising an upper portion of the electrode structure 682. A casing or housing 685 that is generally cylindrical shaped has an upper open end and a lower open end. The upper open end of the casing mates with the perimeter of the lower opening of the bellows. A circuit board 686 and electrode structure that is generally disc shaped is provided within the casing 685, and is positioned near the lower open end of the casing. The circuit board 686 and electrode structure has the electrode on the bottom of the structure, so that it is facing toward the head of the subject in use. A disc shaped pot/seal 687 has a diameter substantially the same as the circuit board 686 and electrode structure, and is provided in the casing 685 on top of the circuit board 686 and electrode structure. Both the circuit board 686 and electrode structure and the pot/seal 687 have an opening extending from the top to the bottom of these respective structures, to allow EEG gel to proceed from the reservoir 683 of the bellows 684 to a location near the electrode at the bottom of the electrode structure 682. The bellows 684 may be removed from the casing 685 to refill the bellows 684 with EEG gel, and then the bellows 684 may be put back into engagement with the casing 685.

Figure 21:
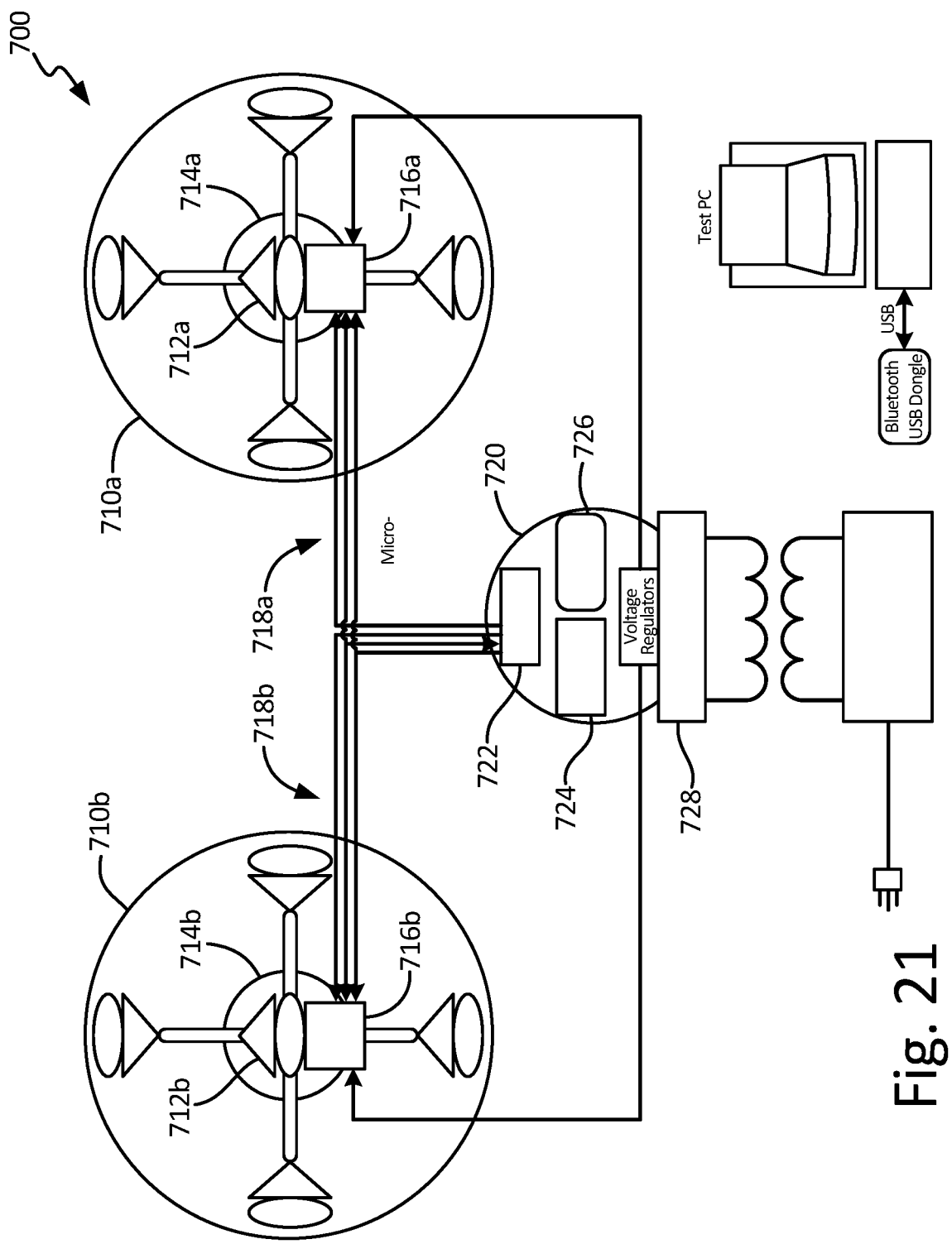
FIG. 21 is a schematic diagram of another type of example electronics that can be used in conjunction with the EEG headsets described herein.

As an alternative to the EEG headset designs described above including only one electrode assembly, multiple electrode assemblies may be utilized for one headset and affixed to one electrode registration assembly at multiple different locations. If that were the case in embodiment 2B, the circuit components may be configured as shown in FIG. 21. As shown, the EEG headset 700 includes two electrode assemblies 710a and 710b, each electrode assembly 710a-b including five electrodes (one central electrode and four peripheral electrodes). As shown, on each of the two electrode assemblies 710a-b, each one of the electrode structures has a local amplifier 712a and 712b provided on the circuit boards 714a and 714b having an electrode attached. Also provided on each of the electrode assemblies 710a-b in this embodiment is an A/D converter component 716a and 716b to convert the sensed analog signals at each of the five electrodes into a digital signal. The amplified and digitized data representative of the sense brain signals is transmitted from the electrode assembly 710a-b via a serial bus line 718a and 718b to a battery/transmitter box 720, which as described previously may be provided near the back of the EEG headset away from the recording site. The battery/transmitter box 720 in this embodiment includes a microcontroller 722, a battery 724, and a wireless transmission module 726 (Bluetooth module in this example). As shown, the battery 724 provided in the EEG headset may be rechargeable by connection to a charger 728.

EEG Headset Embodiment 3

Figure 24:
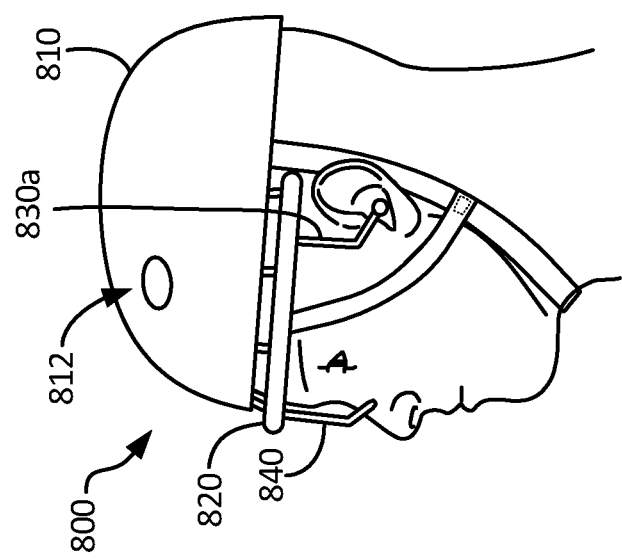
FIG. 24 is a left side view of another example EEG headset, including the portion of FIGS. 22 and 23, in accordance with some embodiments.
Figure 23:
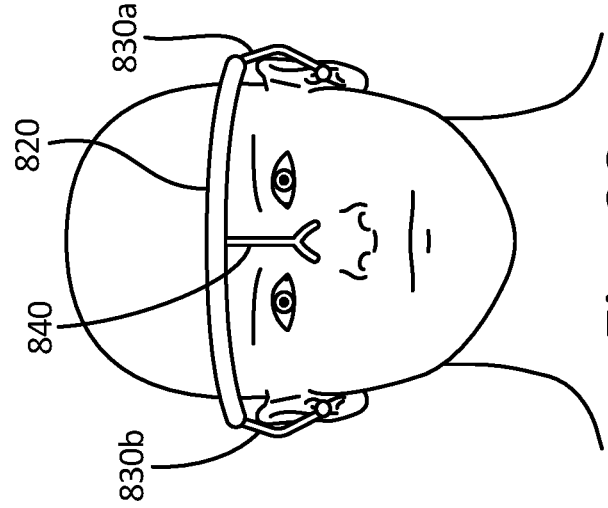
FIG. 23 is a front view of the portion of the EEG headset shown in FIG. 22.
Figure 22:
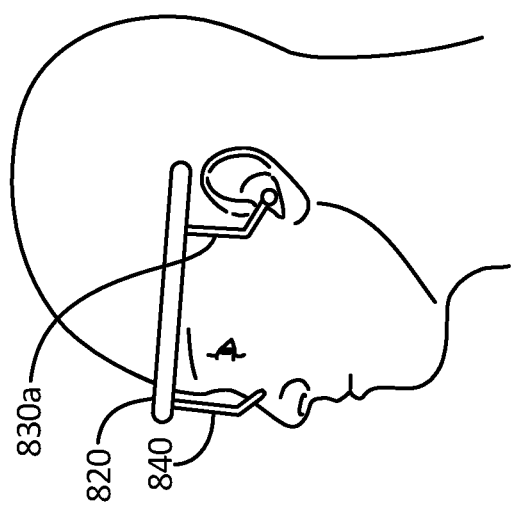
FIG. 22 is a left side view of a portion of another example EEG headset in accordance with some embodiments.

In this embodiment, systems and methods are provided for identifying the EEG site that will be used for BCI application and how that site will be consistently identified for ongoing BCI interactions. The system, as depicted in FIGS. 22-24, consists of two helmets: (1) a screening helmet 800, and (2) a chronic patient helmet 800. While FIG. 24 depicts the design of both the screening helmet 800 and the chronic helmet 800, separate and distinct helmets are contemplated.

The screening helmet 800 consists of four sets of components, (1) a dome 810, (2) an arc 820, (3) an ear interface 830a and 830b, and (4) a nasal interface 840. The dome 810 is the portion of the helmet 800 that covers the head. The screening helmet 800 has a high density of electrodes (not shown) to robustly screen signals and locations on the scalp for a pertinent BCI signal. The arc 820 is a curved bar that is attachable and detachable with the dome 810. The arc 820 when worn extends horizontally and above the eye brows, and terminates at each end at the external auditory canals bilaterally. The arc 820 connects to the head by its variably sized components that fit into the ear (ear interfaces 830a-b) canals and the bridge of the nose or nasion (nasal interface 840).

For the screening helmet 800, the dome 810 may be variably affixed to the arc 820, which may allow, for example, movement of an electrode near a location closest to the ipsilateral signal to be moved even slightly to an optimal position, so that position for the ipsilateral signal on the subject's head may be marked so that an electrode 812 of the chronic helmet may be applied exactly on that point. Additionally there may a number of different sized nasal 840 and ear interfaces 830a-b that allow the dome 810 to best fit the head. The screening arc 820 will have measurement marks to identify the best permanent position of the dome 810 and the ear 830a-b and nasal 840 interfaces.

The chronic patient helmet 800 has an arc 820 that is fixed to the dome 810 and has an ear interface 830a-b and nasal interface 840 that will be set in size and position on the arc 820. When the subject places the helmet 800 on the subject's head, because of the anatomic geometry of the subject's ears and nose, the subject will always have the dome 810 (and the specific electrodes within it) positioned on the exact same location on the head.

A method of use for this system would be as follows. First, a patient presents to have an EEG screening for a stroke rehabilitation BCI system utilizing ipsilateral brain signals. Second, the subject is fitted with the arc 820. The appropriate position of the arc 820 may be, for example, one centimeter above the eye brows, and should terminate above either ear canal bilaterally. To accomplish this, various size ear 830a-b and nose 840 interface sizes may be tested to best achieve this arc position. This may entail ear interfaces 830a-b with different lengths and different angles. Also there may be different locations along the arc 820 that the nasal 840 and ear interfaces 830a-b may be attached. Third, once the arc 820 is appropriately positioned and the various interface sizes and positions are documented, the dome 810 may then be mounted on the head relative to the arc 820. The connection points of the dome 820 relative to the arc 820 are also noted.

Fourth, EEG screening is then performed, as described above in connection with the first EEG headset embodiment (EEG headset 100). Fifth, an electrode location is then defined within the electrode array in the dome 810. Sixth, the customized chronic helmet 800 will then be assembled based on custom specifications from the screening helmet. These configurations may include the following: (a) the size of the nasal interface 840, (b) the size of the ear interfaces 830a-b, (c) the position of the nasal interface 840, (d) the position of the ear interfaces 830a-b, (e) the position of the dome 810 relative to the arc 820, (f) the location within the dome 810 where the chronic electrodes (e.g., electrode 812) should be. Seventh, the chronic helmet 800 will be assembled such that when the patient helmet 800 is donned that it will interface with their ear and nose in such way that the location of the electrode 812 on the scalp will always be the same.

Variations of the third embodiment may include one or more of the following. The dome 810 may either be a solid contiguous dome or it may simply be cross hatched bars. The arc 820 may completely encircle the head. The arc 820 may be a part of the dome 810 in the screening helmet 800 with variable attachments for the ear 830a-b and nasal 840 interfaces. There may be other anatomic landmarks that may be interfaced with on the head (for example, the mastoids). Finally, the screening and chronic helmets 800 may be the same construct but with the ear 830a-b and nasal 840 interfaces being adjustable and lockable in place.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Embodiments and all of the functional operations described in this specification may be implemented in digital electronic circuitry, or in computer software, firmware, or hardware, including the structures disclosed in this specification and their structural equivalents, or in combinations of one or more of them. Embodiments may be implemented as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any form of programming language, including compiled or interpreted languages, and it may be deployed in any form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

While this specification contains many specifics, these should not be construed as limitations on the scope of the disclosure or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described components and systems may generally be integrated together in a single product or multiple products.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A device for recording electrical activity of a subject's brain, comprising:
   an electrode assembly comprising:
      a rigid electrode support structure; and a plurality of body surface electrodes each coupled to the rigid electrode support structure, wherein the rigid electrode support structure maintains the plurality of body surface electrodes in a fixed orientation relative to each other, wherein the plurality of body surface electrodes are configured to acquire an electrical signal present on a surface of a subject's head, the electrical signal being indicative of electrical activity present within a portion of the subject's brain; and a wearable electrode registration assembly having a front head engagement portion configured to engage with the subject's nose and a lateral structure including an ear registration component that is contoured to engage with and rest upon the subject's ear helix root to provide consistent anatomical positioning of the electrode assembly relative to the subject's ear helix root, wherein the rigid electrode support structure is adjustably engaged within a slot defined by the ear registration component such that, when the electrode registration assembly is worn by the subject in a generally fixed orientation with respect to the subject's nose and ear helix root, the electrode assembly is positionally adjustable with respect to the ear registration component along the slot such that positions of the plurality of body surface electrodes with respect to the subject's head are adjustable while the fixed orientation of the plurality of body surface electrodes relative to each other is maintained and while the electrode registration assembly remains in the generally fixed orientation.

2. The device of claim 1, wherein the front head engagement portion is shaped to engage against a particular portion of the subject's nasion.

3. The device of claim 1, wherein the wearable electrode registration assembly comprises an anterior-to-posterior wearable structure configured to be worn over the top of the subject's head and extend from a top of the subject's head, down the subject's forehead, to the front head engagement portion, wherein the anterior-to-posterior wearable structure is further configured to extend from the top of the subject's head, down the back of the subject's head, to a back head engagement portion, and wherein the back head engagement portion comprises an inwardly curved structure having a surface that is shaped complementary with a particular portion of the subject's inion.

4. The device of claim 1, wherein the ear registration component is a first ear registration component that is contoured to engage with and rest upon a first ear helix root of the subject, wherein the lateral structure is configured to extend from the top of the subject's head down both sides of the subject's head, and wherein the lateral structure comprises a second ear registration component that is contoured to engage with and rest upon a second ear root helix of the subject.

5. The device of claim 1, wherein the plurality of body surface electrodes comprises one centrally located electrode and a plurality of peripheral electrodes that are each located on a respective arm of the rigid electrode support structure that laterally extends from the location of the centrally located electrode.

6. The device of claim 1, wherein the wearable electrode registration assembly comprises one or more generally flat strips of deformable material configured to be deformed and retain a configuration having a surface with a shape that generally conforms with a shape of the subject's head.

7. The device of claim 6, wherein the one or more generally flat strips of deformable material comprises thermoplastic material.

8. The method of claim 7, wherein the thermoplastic material comprises ethylene vinyl acetate.

9. The device of claim 8, wherein the front head engagement portion is shaped to engage against a particular portion of the subject's nasion.

10. The device of claim 9, wherein the front head engagement portion comprises an inwardly curved saddle structure having a surface that is shaped complementary with the particular portion of the subject's nasion.

11. The device of claim 1, wherein the wearable electrode registration assembly comprises configurable wire frame structures.

12. The device of claim 11, wherein the wearable electrode registration assembly comprises an anterior-to-posterior structure comprising a first configurable wire frame structure configured to engage the subject's nasion at a front of the subject's head and the subject's inion at a back of the subject's head, and wherein the lateral structure comprises a second configurable wire frame structure.

13. The device of claim 12, wherein the electrode assembly is movable up or down relative to locations on the subject's head by adjusting the second configurable wire frame structure.

14. The device of claim 13, wherein the second configurable wire frame structure of the transverse structure is movable relative to the first configurable wire frame structure forward and backward, thereby adjusting the electrode assembly forward or backward relative to locations on the subject's head.

15. The device of claim 1, wherein the wearable electrode registration assembly comprises:
a dome structure configured to cover the subject's head; and
an arc structure comprising a curved bar attachable and detachable with the dome structure and configured such that, when worn, the arc structure extends horizontally and above the subject's eye brows, and terminates at each end at the subject's external auditory canals bilaterally.

\* \* \* \* \*